US007910090B2

(12) United States Patent
Dueva-Koganov et al.

(10) Patent No.: US 7,910,090 B2
(45) Date of Patent: *Mar. 22, 2011

(54) NON-IRRITATING COMPOSITIONS

(75) Inventors: Olga V. Dueva-Koganov, White Plains, NY (US); James P. SaNogueira, Suffern, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/334,071

(22) Filed: Jan. 18, 2006

(65) Prior Publication Data

US 2006/0286053 A1    Dec. 21, 2006

Related U.S. Application Data

(60) Provisional application No. 60/692,106, filed on Jun. 20, 2005.

(51) Int. Cl.
| A61K 8/00 | (2006.01) |
| A61K 8/02 | (2006.01) |
| A61K 31/765 | (2006.01) |
| A61K 33/42 | (2006.01) |
| A61K 33/24 | (2006.01) |
| A61K 33/22 | (2006.01) |
| A61K 33/14 | (2006.01) |
| A61K 33/00 | (2006.01) |
| A61K 31/69 | (2006.01) |
| A61K 31/235 | (2006.01) |
| A61K 31/19 | (2006.01) |
| A61K 31/195 | (2006.01) |
| A61K 31/17 | (2006.01) |
| A61K 31/155 | (2006.01) |
| A61K 31/14 | (2006.01) |
| A61K 31/075 | (2006.01) |
| A61K 31/045 | (2006.01) |
| A61K 31/05 | (2006.01) |
| A61K 47/00 | (2006.01) |
| A61K 47/30 | (2006.01) |

(52) U.S. Cl. ......... 424/59; 424/60; 424/78.37; 424/401; 424/606; 424/617; 424/659; 424/660; 424/679; 424/680; 424/681; 424/717; 514/64; 514/532; 514/544; 514/557; 514/566; 514/574; 514/588; 514/635; 514/642; 514/643; 514/717; 514/724; 514/731; 514/769; 514/772.3; 514/784; 514/785; 514/788; 514/844; 514/970

(58) Field of Classification Search .................... 424/59, 424/60, 400, 401
See application file for complete search history.

(56) References Cited

U.S. PATENT DOCUMENTS

| 3,415,929 | A | * | 12/1968 | Lachman et al. | ............. 514/157 |
| 4,172,122 | A | | 10/1979 | Kubik | |
| 4,481,186 | A | | 11/1984 | Deckner | |
| 4,707,354 | A | | 11/1987 | Garlen et al. | |
| 4,772,501 | A | | 9/1988 | Johnson et al. | |
| 4,797,272 | A | | 1/1989 | Linn et al. | |
| 4,847,071 | A | | 7/1989 | Bissett et al. | |
| 4,923,693 | A | * | 5/1990 | Michalos | ........................ 424/59 |
| 5,447,715 | A | | 9/1995 | Roberts | |
| 5,518,718 | A | | 5/1996 | Ding et al. | |
| 5,536,502 | A | | 7/1996 | Mulder | |
| 5,560,917 | A | | 10/1996 | Cohen et al. | |
| 5,576,354 | A | | 11/1996 | Deflandre et al. | |
| 5,587,150 | A | | 12/1996 | Deflandre et al. | |
| 5,591,426 | A | * | 1/1997 | Dabrowski et al. | ........ 424/78.04 |
| 5,667,765 | A | | 9/1997 | Hansenne et al. | |
| 5,672,337 | A | | 9/1997 | Ascione et al. | |
| 5,731,005 | A | | 3/1998 | Ottoboni et al. | |
| 5,741,497 | A | | 4/1998 | Guerrero et al. | |
| 5,747,052 | A | | 5/1998 | Mimikos et al. | |
| 5,770,183 | A | | 6/1998 | Linares | |
| 5,788,954 | A | | 8/1998 | Bonda et al. | |
| 5,849,273 | A | | 12/1998 | Bonda et al. | |
| 5,874,576 | A | * | 2/1999 | Huber | ........................... 544/211 |
| 5,876,699 | A | | 3/1999 | DiSomma et al. | |
| 5,888,493 | A | | 3/1999 | Sawaya | |
| 5,922,331 | A | | 7/1999 | Mausner | |
| 5,985,251 | A | | 11/1999 | Gonzenbach et al. | |
| 5,989,528 | A | | 11/1999 | Tanner et al. | |
| 6,033,649 | A | | 3/2000 | Gonzenbach et al. | |
| 6,068,847 | A | * | 5/2000 | Aleles et al. | ................... 424/401 |
| 6,071,501 | A | | 6/2000 | Robinson et al. | |
| 6,159,480 | A | | 12/2000 | Tseng et al. | |
| 6,197,281 | B1 | | 3/2001 | Stewart et al. | |
| 6,231,838 | B1 | | 5/2001 | Morefield et al. | |

(Continued)

OTHER PUBLICATIONS

P. Michalos, E. N. Avila, G. J. Florakis and P. S. Hersh, "Do Human Tears Absorb Ultraviolet Light?", The Contact Lens Association of Ophthamologists Journal (The CLAO Journal), 1994, 20(3), 192-192, Abstract only.*

(Continued)

Primary Examiner — John Pak
Assistant Examiner — Nathan W Schlientz
(74) Attorney, Agent, or Firm — Ohlandt, Greeley, Ruggiero & Perle, L.L.P.

(57) ABSTRACT

The present invention provides a base composition that allows for the formulation of non-irritating cosmetic and/or dermatological compositions. The base composition includes one or more of electrolyte, buffer, mild preservative, lubricant, or any combinations thereof. It is preferred that one or more of the above components are eye-safe and/or eye-compatible. The present invention also provides photoprotective cosmetic and/or dermatological compositions that include the base composition and one or more sunscreen active components and are non-irritating to mammalian eyes.

15 Claims, No Drawings

U.S. PATENT DOCUMENTS

| | | |
|---|---|---|
| 6,280,712 B1 | 8/2001 | Ansmann et al. |
| 6,287,583 B1 | 9/2001 | Warren et al. |
| 6,432,389 B1 | 8/2002 | Hansenne et al. |
| 6,485,713 B1 | 11/2002 | Bonda et al. |
| 6,491,901 B2 | 12/2002 | Gers-Barlag et al. |
| 6,576,248 B1 | 6/2003 | Simardi et al. |
| 6,630,175 B1 | 10/2003 | Shapiro et al. |
| 6,719,964 B1 | 4/2004 | Shapiro et al. |
| 6,838,077 B2 | 1/2005 | Muller |
| 6,887,400 B1 | 5/2005 | Wei et al. |
| 7,022,316 B2 | 4/2006 | Galdi et al. |
| 7,067,479 B2 | 6/2006 | Xia et al. |
| 7,119,059 B2 | 10/2006 | Librizzi et al. |
| 2002/0006418 A1 | 1/2002 | Kung et al. |
| 2003/0039619 A1 | 2/2003 | Bunger et al. |
| 2003/0161795 A1 | 8/2003 | Tsuzuki et al. |
| 2003/0219392 A1 | 11/2003 | Kung et al. |
| 2003/0228267 A1 | 12/2003 | Aust et al. |
| 2004/0052737 A1 | 3/2004 | Hill |
| 2004/0067206 A1 | 4/2004 | Paspaleeva-Kuhn et al. |
| 2004/0166132 A1 | 8/2004 | Shapiro et al. |
| 2004/0228884 A1 | 11/2004 | Gupta |
| 2005/0075256 A1 | 4/2005 | Librizzi et al. |
| 2005/0180933 A1 | 8/2005 | Wei et al. |
| 2005/0186160 A1 | 8/2005 | Aust et al. |
| 2006/0008426 A1 | 1/2006 | Doring et al. |
| 2006/0008427 A1 | 1/2006 | Dueva et al. |
| 2006/0078514 A1 | 4/2006 | Bertz et al. |
| 2006/0093636 A1 | 5/2006 | Farber |
| 2006/0198800 A1 | 9/2006 | Dilallo et al. |

OTHER PUBLICATIONS

Environmental Protection Agency Health Effects Test Guidelines OPPTS 870.2400 Acute Eye Irritation, Aug. 1998.*

* cited by examiner

7,910,090 B2

NON-IRRITATING COMPOSITIONS

RELATED APPLICATION

This application claims the benefit of U.S. Provisional patent Application Ser. No. 60/692,106, filed on Jun. 20, 2005.

BACKGROUND OF THE INVENTION

1. Field of the Invention

The present invention relates generally to non-irritating cosmetic compositions. More particularly, the present invention relates to base compositions for use in formulating non-irritating cosmetic compositions.

2. Description of Related Art

Cosmetic and dermatological compositions are commercially available in various forms, such as lotions, sprays, creams, gels, milks and the like, and are well known in the art. Many of the components, especially active components, used in these compositions can be irritating to the skin and/or eyes. It is common to include one or more sunscreen active components in a cosmetic or dermatological composition to create a photoprotective composition.

Photoprotective compositions, such as sunscreen compositions, are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays. Sunscreen compositions are typically formulated with one or more sunscreen active agents, which absorb and/or block the UVA and UVB radiation. The SPF of the composition is usually controlled by the amount of sunscreen active present in the composition. Generally, the more sunscreen active included in the composition, the higher the SPF.

However, photoprotective compositions are known to cause irritation to the skin and eyes during application and use, due in large part to the inclusion of the one or more organic sunscreen actives in the composition. Prior art compositions have attempted to circumvent this problem by reformulating the photoprotective compositions with little or no organic sunscreen actives and solely or predominantly inorganic sunscreen components, such as titanium dioxide and/or zinc oxide. Examples of sunscreens that only include inorganic sunscreen actives are Tsunami Sun Tearless Sunscreen Lotion SPF 30 and SPF 45 and Karibbean Kidz Sunblock SPF 25. However, predominant or exclusive use of inorganic sunscreen(s) poses significant problems and/or limitations, including, but not limited to, skin whitening, limited UVA protection, cost constraints, and difficulties in formulating compositions with high SPF values.

What is clearly not appreciated in the prior art, yet is unexpectedly achieved by the present invention, is a non-irritating cosmetic photoprotective composition that includes one or more organic sunscreen actives.

SUMMARY OF THE INVENTION

It is an object of the present invention to provide a base composition for use in formulating cosmetic and/or dermatological compositions that are non-irritating to mammalian eyes.

It is another object of the present invention to provide such a base composition that allows for the formulation of photoprotective cosmetic and/or dermatological compositions that are non-irritating to mammalian eyes.

It is yet another object of the present invention to provide such a base composition that allows for the formulation of photoprotective cosmetic and/or dermatological compositions that are non-irritating to mammalian skin.

It is a further object of the present invention to provide such a base composition that includes at least one of electrolyte, buffer, mild preservative, lubricant, or any combinations thereof.

It is still a further object of the present invention to provide a non-irritating photoprotective cosmetic and/or dermatological composition that includes the base composition and one or more sunscreen actives.

To accomplish the foregoing objects and advantages, the present invention, in brief summary, is a base composition that allows for the formulation of non-irritating cosmetic and/or dermatological compositions. The base composition includes one or more of electrolyte, buffer, mild preservative, lubricant, or any combinations thereof. It is preferred that one or more of the above components are eye-safe and/or eye-compatible. The present invention also provides photoprotective cosmetic and/or dermatological compositions that include the base composition and one or more sunscreen active components and are non-irritating to mammalian eyes and/or mammalian skin.

DETAILED DESCRIPTION OF THE INVENTION

The present invention is a base composition that allows for the formulation of non-irritating cosmetic compositions. The base composition includes one or more of electrolyte, buffer, mild preservative, lubricant, or any combinations thereof. It is preferred that one or more of the above components are eye-safe and/or eye-compatible.

The term "non-irritating" in the context of the present invention refers to a condition of a mammalian eye and includes, but is not limited to, non-lacrimating (non-tearing, tear-free); does not induce stinging, burning, or itching; does not induce ocular, bulbar conjunctival irritation, palpebral conjunctival irritation, or any combinations thereof.

The term "cosmetic composition" may include, but is not limited to, the following: sunscreens, dermatological compositions, make-up compositions, make-up removers, cleansers, lotions, gels, creams, sticks, powders, milks, conditioners, sprays, eye-liners, solutions, or serums.

It has been unexpectedly found that the use of the base composition according to the present invention in formulating cosmetic compositions results in a composition that is non-irritating to the eyes of a consumer. The base composition of the present invention is particularly useful in formulating non-irritating photoprotective cosmetic compositions.

The base composition of the present invention includes at least one of the following components: electrolyte, buffer, mild preservative, lubricant, or any combinations thereof. Preferably, the base composition includes at least two of these components and more preferably all four components. It is also preferred that one or more of the above components are eye-safe and/or eye-compatible.

Suitable electrolyte for use in the base composition of the present invention includes, but is not limited to, sodium chloride, potassium chloride, magnesium chloride, disodium EDTA, or any combinations thereof. A preferred electrolyte is sodium chloride. The above components are eye-safe and/or eye-compatible.

The electrolyte may be included in the base composition in an amount between about 10 weight percent (wt. %) to about 100 wt. %, based on the total weight of the base composition. Preferably, it is present in an amount between about 20 wt. % to about 50 wt. % and more preferably between about 30 wt. % to about 40 wt. %, based on the total weight of the base composition.

Suitable buffer for use in the base composition of the present invention includes, but is not limited to, sodium acetate, sodium citrate, trisodium citrate, citric acid, sodium bicarbonate, sodium lactate, trisodium phosphate, disodium phosphate, sodium borate, boric acid, calcium fumarate, sodium succinate, tris-maleate, or any combinations thereof. A preferred buffer is trisodium citrate. The above components are eye-safe and/or eye-compatible.

The buffer may be included in the base composition in an amount between about 1 weight percent (wt. %) to about 100 wt. %, based on the total weight of the base composition. Preferably, it is present in an amount between about 1 wt. % to about 20 wt. % and more preferably between about 3 wt. % to about 10 wt. %, based on the total weight of the base composition.

Suitable mild preservative for use in the base composition of the present invention includes, but is not limited to, esters, phenols, phenoxyethanol, paraben, methyl paraben, butyl paraben, ethyl paraben, propyl paraben, isobutyl paraben, isopropyl paraben, polyquaternium-1, benzalkonium chloride, sorbic acid, potassium sorbate, polyaminopropyl biguanidine, diazolidinyl urea, or any combinations thereof. Preferably, the preservative is a combination of phenoxyethanol, methyl paraben, butyl paraben, ethyl paraben, propyl paraben, and isobutyl paraben sold under the tradename PHENONIP by Clariant. The above components are eye-safe and/or eye-compatible.

The mild preservative may be included in the base composition in an amount between about 5 wt. % to about 100 wt. %, based on the total weight of the base composition. Preferably, it is included in an amount between about 10 wt. % to about 35 wt. % and more preferably between about 15 wt. % and 28 wt. %, based on the total weight of the base composition.

Suitable lubricant that may be used in the base composition of the present invention includes, but is not limited to, polyols, glycerin, propylene glycol, polypropylene glycol, PEG-400, PEG-8, or any combinations thereof. Preferably, the lubricant is selected from the group consisting of glycerin, PEG-8, PEG-400, or any combinations thereof. The above components are eye-safe and/or eye-compatible.

The lubricant may be included in the base composition of the present invention in an amount between about 10 wt. % to about 100 wt. %, based on the total weight of the base composition. Preferably, the lubricant is present in an amount between about 25 wt. % to about 60 wt. % and more preferably between about 35 wt. % to about 50 wt. %, based on the total weight of the base composition.

Optional components that are suitable for inclusion in or with the base composition include, for example, one or more buffer, nonionic surfactant, protein, glucoprotein, polar lipid, amino acid, glycin, polymer, sodium bisulfite, sodium metabisulfite, thiourea, cellulose derivatives such as hydroxypropylmethylcellulose, hydroxyethylcellulose and methylcellulose, polyvinyl alcohol, polyvinylpyrrolidone, sorbitol, mannitol, linoleic acid ester, hepes linoleate, or any combinations thereof. Hydroxypropylmethylcellulose, methylcellulose, and/or polyvinyl alcohol may increase viscosity and also provide some lubricating effect.

Not intended to be bound by theory, it is believed that the use of the base composition according to the present invention in formulating a cosmetic composition results in the cosmetic composition having physiological conditions similar to those of a mammalian eye. As a result, cosmetic compositions formulated with the base composition of the present invention are non-irritating to the eye.

At least three known properties, namely tonicity (osmolarity), buffer capacity, and pH are associated with the use of the base composition of the present invention in cosmetic compositions that result in the cosmetic composition having similar physiological conditions and properties to that of a mammalian eye.

Osmolarity is a measure of the osmotic pressure generated by a solution across a perfect semi-permeable membrane, which allows free passage of water and prevents movement of solute compared to water. Osmolarity is dependent on the number of particles in solution but independent of the nature of the particles.

Tonicity is a measure of the osmotic pressure that a substance can exert across a cell membrane, compared to biological fluid, for example natural tears or plasma. Tear fluid has an osmolarity of about 0.3 osm/l, therefore a 0.15 mol/l NaCl or 0.9% NaCl solution may be said to be isotonic with tear fluids.

Tonicity (osmolarity) is very important for eye comfort. Agent used to adjust osmolarity may be NaCl and/or mannitol. Like plasma, lacrimal fluids generally have the tonicity of normal (0.9%) saline. A wider range of NaCl equivalency of about 0.5 to about 2% may also be acceptable.

Solutions containing the same concentration of particles and thus exerting equal osmotic pressures are called isoosmotic. A 0.9% solution of NaCl (saline) is isoosmotic with blood and tears. The term isotonic, meaning equal tone, is used interchangeably with the term isoosmotic.

The osmolarity of the water phase of the cosmetic composition, which is also directly influenced by the use of the base composition of the present invention, should be between about 175 mOsm/kg and about 700 mOsm/kg. This means that electrolyte and buffer should be included in such an amount that can create an osmotic pressure similar to the osmotic pressure created by about 0.5% to about 2% of sodium chloride solution in the water phase of the product or in a final formulation (product). Assuming that the water phase is included from about 30% to about 90% in the final product, a cosmetic composition with the base composition and a water phase osmolarity mentioned above is well-tolerated and non-irritating to the eyes of a consumer.

The pH of the water phase of the cosmetic composition, which is directly influenced by the use of the base composition of the present invention, should be between about 5.5 and about 8.5. More preferably, the pH range is from about 6.0 to about 7.6. As a result, a cosmetic composition with the base composition and a water phase pH between about 6.0 and about 7.6 resembles physiological conditions of lacrimal fluids and is well tolerated and non-irritating to the eyes of a consumer. Knowing the optimal pH of a product, a mechanism for adjusting and maintaining the pH of the solution is needed.

Buffer capacity is a measure of the efficiency of a buffer in resisting changes in pH. Buffer capacity is expressed as the amount of strong acid or base, in gram-equivalents, that must be added to 1 liter of the solution to change its pH by one unit.

A buffer or buffer system may include buffer salts alone or in conjunction with acids. Salts of weak acids such as trisodium citrate, sodium lactate, trisodium phosphate are suitable buffer salts. Different combinations of acids and salts may also be used as buffers. Buffers reduce the variation in the pH of the product or its water phase.

Buffer capacity of a water phase should allow rapid readjustment of tear fluids to physiological pH upon contact with the product and can be in the range from about 0.002 to about 0.05, more preferably from about 0.004 to about 0.01.

In a preferred embodiment of the present invention the base composition includes about 30 wt. % to about 40 wt. % eye-safe electrolyte; about 3 wt. % to about 10 wt. % eye-safe buffer; about 15 wt. % to about 28 wt. % mild preservative; and about 35 wt. % to about 50 wt. % eye-safe lubricant, based on the total weight of the base composition. A cosmetic composition formulated with this base composition preferably has a buffer capacity, water-phase pH and water-phase osmolarity as described above.

While it should be understood based on the above disclosure that the base composition may be used to formulate any non-irritating cosmetic composition, the invention is described below in more detail in the context of formulating a photoprotective cosmetic composition, which are notorious for being irritating to mammalian eyes due in large part to the use of organic sunscreen actives. The disclosure below is in no way meant to limit the scope of the present invention.

As detailed below, it has been unexpectedly found that a sunscreen composition including the base composition of the present invention can also be formulated with organic sunscreen actives, inorganic sunscreens, or any combinations thereof and yet be non-irritating to the eye. As a result, non-irritating sunscreen compositions with desirable high SPF can be easily formulated that overcome all prior art drawbacks and complications associated with formulating a tear-free sunscreen composition.

Also unexpectedly found, the non-irritating sunscreen compositions formulated with the base composition of the present invention are not only tear-free (non-lacrimating), they do not cause any significant sting, bulbar irritation or palpebral irritation to a mammalian eye.

When used to formulate a photoprotective cosmetic composition and/or sunscreen composition, the base composition of the present invention, as described above, may be present in an amount about 0.5 wt. % to about 10 wt. %, based on the total weight of the cosmetic composition. Preferably, it is present in an amount about 1 wt. % to about 6 wt % and more preferably in an amount about 2 wt. % to about 4 wt. %, based on the total weight of the cosmetic composition.

In addition to the base composition, a sunscreen composition may include one or more of the following additional components: pharmaceutically acceptable carrier, emulsifier, emollient, skin-feel additive, moisturizing agent, film former/waterproofing agent, pH adjuster/chelating agent, preservative, carotenoid, or any combinations thereof.

One or more sunscreen agents may be used in the present invention must be capable of absorbing or blocking the harmful effects of ultraviolet radiation. In addition, they must be non-toxic and non-irritating when applied to the skin. Suitable sunscreen agents that may be used in the sunscreen composition include, but are not limited to, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, or any combinations thereof.

The preferred sunscreen agents are octyl methoxycinnamate, octyl salicylate, homosalate, titanium dioxide, or any combinations thereof. In a preferred embodiment, the use of benzophenones is explicitly excluded.

The one or more sunscreen agents are included in the present composition in an amount about 1 weight percent (wt. %) to about 40 wt. %, based on the total weight of the composition. Preferably, the one or more sunscreen agents are included in an amount about 4 wt. % to about 35 wt. % to achieve a SPF of about 2 to about 50. More preferably, they are present in an amount between about 20 wt. % to about 35 wt. % to achieve a SPF of about 30 to about 50.

Suitable emulsifiers that may be used in the sunscreen composition include, but are not limited to, butylated PVP, cetyl alcohol, cetyl dimethicone copolyol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, sodium glyceryl oleate phosphate, hydrogenated vegetable glycerides phosphate, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or any combinations thereof. Preferred emulsifier is cetyl dimethicone copolyol.

The amount of emulsifier present in the sunscreen composition is about 1 wt. % to about 15 wt. % of the total weight of the composition. Preferably, the emulsifier is present in an amount about 2.5 wt. % to about 7.5 wt. % of the total weight of the composition.

The sunscreen composition may also include water. Water is present in an amount about 45 wt. % to about 75 wt. %, and preferably about 50 wt. % to about 65 wt. %, of the total weight of the sunscreen composition.

The sunscreen composition may include one or more emollients. An emollient provides a softening or soothing effect on the skin surface and is generally considered safe for topical use. It also helps control the rate of evaporation and the tackiness of the sunscreen composition.

Suitable emollients include, but are not limited to, cyclomethicone, dimethicone, dicapryl maleate, caprylic/capric triglyceride, mineral oil, lanolin oil, coconut oil, cocoa butter, olive oil, aloe extracts such as aloe vera, aloe barbadensis leaf juice, jojoba oil, castor oil, fatty acid such as oleic and stearic, fatty alcohol such as cetyl and hexadecyl (ENJAY), diisopropyl adipate, hydroxybenzoate esters, benzoic acid esters of $C_9$-$C_{15}$ alcohols, isononyl iso-nonanoate, alkanes such as mineral oil, silicone such as dimethyl polysiloxane, ether such as polyoxypropylene butyl ether and polyoxypropylene cetyl ether, $C_{12}$-$C_{15}$ alkyl benzoate, isohexadecane, dibutyl adipate, or any combinations thereof. Preferred emollients are isohexadecane, dibutyl adipate, aloe vera, or any combinations thereof.

The total amount of emollient present in the sunscreen composition is typically about 0.10 wt. % to about 30 wt. %, based on the total weight of the composition. The preferred amount of emollient is about 1 wt. % to about 20 wt. %, with about 5 wt. % to about 10 wt. % being more preferred.

The feel of the sunscreen composition upon application to the skin may be a consideration of a consumer when purchasing a sunscreen. Moreover, a smooth, silky sunscreen composition may be more uniformly applied over the skin. To further enhance the feel of the sunscreen compositions of the present invention when applied to the skin, a skin-feel additive may be included. Suitable skin-feel additives include, but are not limited to, synthetic polymers, silicones, esters, particulates, or any combinations thereof.

Skin-feel additive may be present in the sunscreen composition in an amount about 0.10 wt. % to about 5 wt. %, based on the total weight of the composition. More preferably, it is present in an amount about 0.30 wt. % to about 0.70 wt. % of the total weight of the composition.

The pH of the compositions of the present invention may be adjusted by one or more basic pH adjusters and/or chelating agents. For example, sodium hydroxide, triethanolamine, disodium EDTA, trisodium EDTA, or any combinations thereof are suitable pH adjusters/chelating agents that may be included in the sunscreen compositions of the present invention.

An effective amount of a pH adjuster and/or chelating agent that may be included to adjust the pH of the final composition to about 5 to about 9. Preferably, the pH is adjusted to about 6 to about 7.6.

A moisturizing agent, such as a humectant, may be used in the compositions of the present invention. Suitable humectants include, but are not limited to, pentylene glycol, caprylyl glycol, butylene glycol, hexylene glycol, or any combinations thereof.

One or more moisturizing agents are optionally included in the compositions of the present invention in an amount about 0.1 wt. % to about 1 wt. % of the total weight of the composition. Preferably, about 0.25 wt. % to about 0.75 wt. % of one or more moisturizing agents may be used in the composition.

Another component that may be used in a sunscreen composition of the present invention is a film former/waterproofing agent. The film former/waterproofing agent is a hydrophobic material that imparts film forming and waterproofing characteristics to an emulsion. One such agent is polyethylene, which is available from New Phase Technologies as PERFORMALENE® 400, a polyethylene having a molecular weight of 400. Another suitable water-proofing agent is polyethylene 2000 (molecular weight of 2000), which is available from New Phase Technologies as PERFORMALENE® 2000. Yet, another suitable film former/waterproofing agent is synthetic wax, also available from New Phase Technologies as PERFORMA® V-825. Another suitable film former/waterproofing agent is C30-38 olefin/isopropyl maleate/MA copolymer, which is available from New Phase Technologies as PERFORMA V-1608. One or more film formers/waterproofing agents may be present in a composition of the present invention in an amount about 0.1 wt. % to about 5 wt. %, based on the total weight of the composition.

Carotenoids may also be present in the sunscreen composition. Carotenoids suitable for use in the present invention include, but are not limited to, one or more lutein, lutein esters, xanthophylls, alpha-carotene, beta-carotene, gamma-carotene, lycopene, zeaxanthin, isozeaxanthin, astaxanthin, canthaxanthin, tanaxanthin, cryptoxanthin, rhodoxanthin, capxanthin, or any combinations thereof. Preferably, the one or more carotenoids are one or more lutein, lutein esters, or any combinations thereof.

Carotenoid may be present in an amount about 0.00001 wt. % to about 0.03 wt. %, based on the total weight of the sunscreen composition. Preferably, the carotenoid may be present in an amount about 0.00001 wt. % to about 0.02 wt. %, and more preferably in an amount about 0.00001 wt. % to about 0.011 wt. %.

The sunscreen compositions of the present invention may also include other optional additives. For instance, photostabilizers, SPF and PFA boosters, for example, caprylyl glycol, one or more fragrances, colorants, plant extracts, absorbents, thickeners, waxes, salicylic acid, alpha and beta hydroxy acids, vitamins including vitamins A, C, and E, retinol, retinol palmitate, vitamin E acetate, tocopherol, vitamin A palmitate, vitamin E palmitate, or any combinations thereof, may be included in the sunscreen compositions.

The above components may be combined to form a stable water-in-oil emulsion, oil-in-water emulsion or dispersion. In a preferred embodiment the sunscreen composition is formulated as a water-in-oil emulsion.

In one preferred embodiment of the present invention, the sunscreen composition includes about 2.5 wt. % to about 3 wt. % base composition and about 20 wt. % to about 35 wt. % of one or more sunscreen agents selected from the group consisting of: octyl methoxycinnamate, octyl salicylate, homosalate, titanium dioxide, or any combinations thereof. Preferably, the sunscreen composition is formulated as a water-in-oil emulsion, wherein the base composition is included in the water phase and the water phase has a ph of about 5.8 to about 8, and an osmolarity between about 175 to about 330. The resulting sunscreen composition does not induce ocular irritation, stinging and/or lacrimation in mammalian eyes.

This unexpected benefit of including the base composition of the present invention in a sunscreen composition is demonstrated in the Examples below.

EXAMPLES

Numerous commercially available sunscreens were tested to evaluate the potential to induce ocular irritation, stinging, and/or lacrimation to the eye.

TABLE 1

Commercially Available Sunscreens

| Commercial Sunscreen (CS) | Commercial Name |
|---|---|
| CS1 | Banana Boat Surf SPF 30 |
| CS2 | Banana Boat Vitaskin SPF 30 |
| CS3 | Banana Boat Ultra Sunblock SPF 30 |
| CS4 | Banana Boat Baby Magic SPF 50 Sunblock Lotion |
| CS5 | Neutrogena Sensitive Skin Sunblock Lotion SPF 30 |
| CS6 | Banana Boat Baby Magic SPF 50 Instant Protection |
| CS7 | Suntanicals Sunscreen Lotion SPF 30 |
| CS8 | Vitaskin SPF 50 |
| CS9 | Coppertone Kids SPF 30 |
| CS10 | Coppertone Water Babies SPF 45 |
| CS11 | Coppertone Water Babies SPF 50 Spectra |
| CONTROL | Sterile Water |

TABLE 2

Commercial Sunscreen Components

| Sunscreen Active | CS1 (wt %) | CS2 (wt %) | CS3 (wt %) | CS4 (wt %) | CS5 (wt %) | CS6 (wt %) | CS7 (wt %) | CS8 (wt %) | CS9 (wt %) | CS10 (wt %) | CS11 (wt %) |
|---|---|---|---|---|---|---|---|---|---|---|---|
| Octisalate | 5 | 5 | 4.75 | 5 | | 4.75 | 5 | 5 | * | * | * |
| Oxybenzone | 6 | 3 | 5.25 | 6 | | 6 | 4.1 | 4.5 | * | * | * |
| Homosalate | | | | | | | | | * | * | * |
| Octinoxate | | 7.5 | 7.5 | 7.5 | | | 7.5 | 7.5 | * | * | * |
| Avobenzone | | 1 | | | | | 1.5 | | * | | |
| Octocrylene | | | | 10 | | | | | | | * |
| Titanium Dioxide | 3 | | 1.2 | | * | 1.2 | | | | | |
| Zinc Oxide | | | | | | | | 7.5 | | | * |

\* These components are known to be present in these commercial sunscreens, but the exact amount is unknown Eye instillation studies of the commercial sunscreens listed in Table 1 were conducted in order to evaluate their potential to induce ocular irritation, sting, and/or lacrimation in human subjects according to the protocol set forth below that is appropriate for cosmetic/OTC test materials:

Each test material must pass USP sterility testing prior to initiation of the study. The control is sterile distilled water. Other suitable controls that may be used include, but are not limited to, isotonic saline solution or any other solution that physiologically resembles mammalian tears. For liquids, a new sterile disposable eyedropper will be used for each product and disposed of immediately after being used. For lotions, new sterile disposable cotton tipped applicator will be used for each product and immediately disposed of after being used.

Panels consist of 10-20 human subjects and are employed in controlled, double-blind, randomized studies. All subjects must have ocular sting, lacrimation, bulbar conjunctiva irritation and palpebral conjunctiva irritation scores of zero (0) at the time the study begins. The scoring system is presented below.

Test materials are instilled into the eyes of the subjects by one individual, and eye examinations are made by the Ophthalmological Investigator. The subject and Ophthalmological Investigator are unaware of which eye is treated with which Test Material and of the previous assessment scores. Eyes are examined by the Ophthalmological Investigator immediately before treatment according to the scoring system. One drop or swab of the appropriate solution/material (temperature 36° C.) is instilled into the right eye of the subject followed by instillation of the appropriate test material or control into the left eye, as per the randomization schedule. All instillations are performed by one trained technician. Two tissues (one for each eye) is provided to blot any excess that falls from the eye.

Within 30 seconds following instillation, eyes are examined and scored according to the scoring system. The eyes are examined and scored again at 5 minutes, followed by the washing of the eyes to flush them out. Eyes are examined and scored again at 15 minutes and 60 minutes post-instillation. If persistent conjunctivitis or other treatment-related adverse symptoms are noted at the 1 hour examination, the subject's eye(s) are washed and examined at 10-15 minute intervals until the condition clears. In the event that symptoms still persist at 2 hours, the subject is re-examined at 24-hour intervals until the symptoms have dissipated.

Scoring System: It should be noted that in evaluating reactions, if the sterile distilled water control elicits a reaction identical to that elicited by the test material, it is judged that the reaction is due to "mechanical irritation" rather than to any chemical component.

Lacrimation:
  0=Within normal limits
  1=Excessive wetness (no distinct tears)
  2=A few formed tears (contained in orbit)
  3=Intense tearing (leaving orbit)
Sting (pain, smarting, etc.):
  0=Within normal limits
  1=Mild, very slight
  2=Moderate
  3=Severe
Bulbar Conjunctiva Irritation:
  0=Within normal limits
  1=Mildly pink
  2=Moderately pink, some dilation
  3=Intense red vessels, dilated
Palpebral Conjunctiva Irritation:
  0=Within normal limits
  1=Mildly pink
  2=Moderately pink
  3=Cherry to deep red Test results are presented in Tables 3-6 (paired difference two tailed t-test was used to determine the significance of the difference between test article and control). Scores that are not significantly different ($p > 0.05$) than that of the control are indicated in the tables as not significant (n.s.)

TABLE 3

Lacrimation: Commercial Product (Control) - Mean Values

| Commercial Sunscreen | 30 sec | 5 min | 15 min | 1 hr |
|---|---|---|---|---|
| CS1 | 0.3 (0.2) n.s. | 0 (0) | 0 (0) | 0 (0) |
| CS2 | 0.5 (0) sig. | 0 (0) | 0 (0) | 0 (0) |
| CS3 | 1.2 (0) sig. | 0.1 (0) n.s. | 0 (0) | 0 (0) |
| CS4 | 1.3 (0) sig. | 0 (0) | 0 (0) | 0 (0) |
| CS5 | 0.4 (0.1) n.s. | 0 (0) | 0 (0) | 0 (0) |
| CS6 | 0.5 (0) sig. | 0.3 (0) n.s. | 0 (0) | 0 (0) |
| CS7 | 0.6 (0.1) sig. | 0 (0) | 0 (0) | 0 (0) |
| CS8 | 1.1 (0.4) sig. | 0 (0) | 0 (0) | 0 (0) |
| CS9 | 0.4 (0) sig. | 0 (0) | 0 (0) | 0 (0) |
| CS10 | 0.9 (0) sig. | 0 (0) | 0 (0) | 0 (0) |
| CS11 | 0.4 (0) sig. | 0 (0) | 0 (0) | 0 (0) |

TABLE 4

Sting: Commercial Product (Control) - Mean Values

| Commercial Sunscreen | 30 sec | 5 min | 15 min | 1 hr |
|---|---|---|---|---|
| CS1 | 1.0 (0) sig. | 0.3 (0) n.s. | 0 (0) | 0 (0) |
| CS2 | 0.9 (0.1) sig. | 0.1 (0) n.s. | 0.1 (0) n.s. | 0 (0) |
| CS3 | 1.0 (0) sig. | 0.3 (0) n.s. | 0.3 (0) n.s. | 0 (0) |

TABLE 4-continued

Sting: Commercial Product (Control) - Mean Values

| Commercial Sunscreen | 30 sec | 5 min | 15 min | 1 hr |
|---|---|---|---|---|
| CS4 | 1.3 (0) sig. | 0.3 (0) sig. | 0.2 (0) n.s. | 0 (0) |
| CS5 | 0.6 (0) sig. | 0.1 (0) n.s. | 0 (0) | 0 (0) |
| CS6 | 0.8 (0.1) sig. | 0.4 (0) sig. | 0 (0) | 0 (0) |
| CS7 | 1.1 (0) sig. | 0 (0) | 0 (0) | 0 (0) |
| CS8 | 1.2 (0) sig. | 0.1 (0) n.s. | 0 (0) | 0 (0) |
| CS9 | 0.9 (0) sig. | 0 (0) | 0 (0) | 0 (0) |
| CS10 | 1.4 (0) sig. | 0.1 (0) n.s. | 0 (0) | 0 (0) |
| CS11 | 0.9 (0) sig. | 0.1 (0) n.s. | 0 (0) | 0 (0) |

TABLE 5

Bulbar Conjunctiva Irritation: Commercial Product (Control) - Mean Values

| Commercial Sunscreen | 30 sec | 5 min | 15 min | 1 hr |
|---|---|---|---|---|
| CS1 | 0.7 (0.4) n.s. | 0.5 (0.1) sig. | 0.4 (0) sig. | 0 (0) |
| CS2 | 0.7 (0.2) sig. | 0.2 (0) n.s. | 0.1 (0) n.s. | 0 (0) |
| CS3 | 0.8 (0.2) sig. | 0.6 (0) sig. | 0.3 (0) n.s. | 0.2 (0) n.s. |
| CS4 | 1.0 (0.2) sig. | 0.5 (0) sig. | 0.3 (0) n.s. | 0.1 (0) n.s. |
| CS5 | 0.8 (0.2) sig. | 0.2 (0) n.s. | 0.2 (0) n.s. | 0 (0) |
| CS6 | 0.8 (0.1) sig. | 0.6 (0) sig. | 0.3 (0) n.s. | 0 (0) |
| CS7 | 0.9 (0.3) sig. | 0 (0) | 0 (0) | 0 (0) |
| CS8 | 1.0 (0.7) n.s. | 0.7 (0) sig. | 0.4 (0) sig. | 0 (0) |
| CS9 | 0.8 (0.3) sig. | 0 (0) | 0 (0) | 0 (0) |
| CS10 | 1.0 (0.2) sig. | 0.4 (0) sig. | 0 (0) | 0 (0) |
| CS11 | 0.8 (0.4) sig. | 0.2 (0) n.s. | 0.1 (0) n.s. | 0 (0) |

TABLE 6

Palpebral Conjunctiva Irritation: Commercial Product (Control) - Mean Values

| Commercial Sunscreen | 30 sec | 5 min | 15 min | 1 hr |
|---|---|---|---|---|
| CS1 | 0.7 (0.4) n.s. | 0.5 (0.1) sig. | 0.4 (0) sig. | 0 (0) |
| CS2 | 0.7 (0.2) sig. | 0.1 (0) n.s. | 0 (0) | 0 (0) |
| CS3 | 0.8 (0.2) sig. | 0.6 (0) sig. | 0.3 (0) n.s. | 0.2 (0) n.s. |
| CS4 | 1.0 (0.2) sig. | 0.4 (0) sig. | 0.3 (0) n.s. | 0.1 (0) n.s. |
| CS5 | 0.8 (0.2) sig. | 0.2 (0) n.s. | 0.2 (0) n.s. | 0 (0) |
| CS6 | 0.8 (0.1) sig. | 0.6 (0) sig. | 0.2 (0) n.s. | 0 (0) |
| CS7 | 0.9 (0.3) sig. | 0 (0) | 0 (0) | 0 (0) |
| CS8 | 1.0 (0.7) n.s. | 0.7 (0) sig. | 0.3 (0) n.s. | 0 (0) |
| CS9 | 0.8 (0.3) sig. | 0 (0) | 0 (0) | 0 (0) |
| CS10 | 1.0 (0.2) sig. | 0.4 (0) sig. | 0 (0) | 0 (0) |
| CS11 | 0.8 (0.4) sig. | 0.2 (0) n.s. | 0.1 (0) n.s. | 0 (0) |

The results indicate that all commercially available sunscreens tested have produced statistically significant lacrimation (tearing) reaction and stinging accompanied by bulbar conjunctiva irritation and palpebral conjunctiva irritation reactions after 30 sec and/or 5 min after eye-instillation. In some instances these reactions were Score 2 level of reactions for Sting and some of reactions persisted for 5 min or even longer.

Additional testing was attempted on commercially available Tsunami Tearless SPF 30 and SPF 45 compositions, both of which only include inorganic sunscreen active components, namely titanium dioxide and zinc oxide. Consistent with the above test protocols, the Tsunami Sun compositions were first evaluated through pre-clinical tests, prior to human tests. While these compositions passed the pre-clinical tests during the first evaluation, they failed pre-clinical tests during the second evaluation, which precluded their second evaluation in human eye instillation studies.

Also tested was a SPF 30 sunscreen formulation formulated by Pugliese Pharmaceuticals, which contained both organic and inorganic sunscreen actives (avobenzone-2.5%, octinoxate-6.5%, octisalate-4%, titanium dioxide-1.6%). While this composition demonstrated tear-free properties, a sting score of 2 (moderate stinging) was generated by this composition.

TABLE 7

Sunscreen compositions formulated with the base composition according to the present invention (PS)

| COMPONENTS | PS1 SPF 50+ (wt. %) | PS2 SPF 30+ (wt. %) |
|---|---|---|
| Sunscreen Active | | |
| Octisalate | 5 | 5 |
| Octinoxate | 7.5 | 7.5 |
| Homosalate | 15 | 9 |
| Titanium Dioxide* | 3 | 1.5 |
| Electrolyte | | |
| Sodium Chloride | 0.9 | 0.9 |
| Sodium EDTA | 0.1 | 0.1 |
| Buffer System | | |
| Trisodium Citrate Dihydrate | 0.17 | 0.17 |
| Preservative | | |
| PHENONIP[1] | 0.5 | 0.75 |
| Lubricant | | |
| PEG-8 | 1 | 1 |
| Glycerin | 0.2 | 0.2 |

*Titanium dioxide used contains 80% of Titanium Dioxide and 20% of coating
[1] phenoxyethanol (and) methylparaben (and) butylparaben (and) ethylparaben (and) propylparaben (and) isobutylparaben Eye instillation studies of sunscreens that represent the preferred art were conducted in order to evaluate their potential to induce ocular irritation, sting, and/or lacrimation (tearing) in human subjects according to the protocol mentioned above.

Test results are presented in Tables 8-11. Paired difference two tailed t-test was used to determine the significance of the difference between test article and control (sterile water).

TABLE 8

Lacrimation: Product (Control) - Mean Values

|  | 30 sec | 5 min | 15 min | 1 hr |
|---|---|---|---|---|
| PS1* | 0 (0) | 0 (0) | 0 (0) | 0 (0) |
| PS2 | (0) | 0 (0) | 0 (0) | 0 (0) |

TABLE 9

Sting: Product (Control) - Mean Values

|  | 30 sec | 5 min | 15 min | 1 hr |
|---|---|---|---|---|
| PS1* | 0 (0) | 0 (0) | 0 (0) | 0 (0) |
| PS2 | 0.2 (0.1) n.s. | 0.1 (0) n.s. | 0 (0) | 0 (0) |

TABLE 10

Bulbar Conjunctiva Irritation: Product (Control) - Mean Values

|  | 30 sec | 5 min | 15 min | 1 hr |
|---|---|---|---|---|
| PS1* | 0.2 (0.2) n.s. | 0.1 (0) n.s. | 0 (0) | 0 (0) |
| PS2 | 0.4 (0.4) n.s. | 0 (0) | 0 (0) | 0 (0) |

TABLE 11

Palpebral Conjunctiva Irritation: Product (Control) - Mean Values

|  | 30 sec | 5 min | 15 min | 1 hr |
|---|---|---|---|---|
| PS1* | 0.2 (0.2) n.s. | 0.1 (0) n.s. | 0 (0) | 0 (0) |
| PS2 | 0.4 (0.4) n.s. | 0 (0) | 0 (0) | 0 (0) |

*20 subject panel

The results clearly indicate that sunscreen compositions formulated with the base composition according to the present invention do not produce a lacrimation (tearing) reaction. They also do not generate statistically significant stinging, bulbar conjunctiva irritation or palpebral conjunctiva irritation compared to the Control (sterile water) at all time intervals after the eye instillation. They also do not generate Score 2 reactions. Therefore, it is preferred that cosmetic compositions that include the base composition according to the present invention achieve a score of less than 1 on all eye instillation studies at 30 sec., such as those noted above. It is more preferred that a cosmetic composition with the base composition of the present invention achieve the following eye instillation scores at 30 sec.: zero lacrimation; less than about 0.2 sting; less than about 0.4 Bulbar Conjunctiva irritation; and less than about 0.4 Palpebral Conjunctiva irritation.

Another attribute of a cosmetic composition formulated with the base composition of the present invention is skin mildness. It has been found that cosmetic compositions formulated with the base composition have cumulative skin irritation scores or Cumulative Irritation Total (CIT) of less than about 35 in a 14 day cumulative irritancy evaluation or cumulative patch test.

Skin cumulative irritancy potentials of the compositions of present invention (PS1 and PS2) were assessed in a 14-day cumulative irritation patch test in 28 subjects, male and female ranging in age from 20 to 73 years. The upper back between the scapulae served as the treatment area. Approximately 0.2 g of test material was applied to the ¾×¾ inch absorbent pad portion of an adhesive dressing (manufactured by TruMed Technologies, Inc., Burnsville, Minn.). These were then applied to the appropriate treatment sites to form occluded patches.

Each composition was applied to the appropriate treatment site Monday through Friday to maintain fourteen (14) consecutive days of direct skin contact. Patches applied on Friday remained in place until the following Monday. Evaluations of the test sites were conducted prior to each patch application. If a test site had been observed to exhibit an evaluation score of "3", the application of test material would have been discontinued and the observed score of "3" would be recorded for the remaining study days.

Evaluation scores:
  0—No visible skin reaction;
  +—Barely perceptible or spotty erythema;
  1—Mild erythema covering most of the test site;
  2—Moderate erythema, possible evidence of mild edema;
  3—Marked erythema, possible edema;
  4—Severe erythema, possible edema, vesiculation, bullae and/or ulceration.

A 14-day Cumulative Irritation Total (CIT) score for each panelist was determined, as were the irritation scores obtained on a daily basis. The CIT enables a ranking of the test articles according to the least to the most irritation under the test conditions described. The maximum possible CIT score of 1120 was calculated by the following equation: (10[# of observations]×28[# of Completing subjects]×4[maximum irritation score]=1120).

A test CIT Score of 0 to 49 indicates mild material, no experimental irritation, with essentially no evidence of cumulative irritation under conditions of use. Table 12 summarizes the comparative CIT scores obtained for PS1 and PS2.

TABLE 12

Cumulative Irritation Total (CIT) Scores

|  | CIT Score |
|---|---|
| PS1 | 24 |
| PS2 | 32.5 |

Under the condition of this study, PS1 and PS2 both achieved a CIT score of less than 49, as they did not indicate a potential for cumulative dermal irritation.

Having thus described the present invention with particular reference to preferred embodiments thereof it will be apparent that various changes and modifications may be made therein without departing from the spirit and scope of the present invention.

What is claimed is:

1. A non-irritating photoprotective cosmetic composition comprising:
  a water phase comprising a base composition having a buffer, an electrolyte, a mild preservative, and a lubricant; and
  one or more sunscreen agents, present in an amount of 4 wt % to 35 wt %, based on the total weight of the photoprotective cosmetic composition, wherein said one or more sunscreen agents is selected from the group consisting of octyl methoxycinnamate, octyl salicylate, homosalate, titanium dioxide, and any combinations thereof,
  wherein said base composition is present in an amount of 2 wt % to 4 wt %, based on the total weight of the photoprotective cosmetic composition,
  wherein said buffer is present in an amount of 3 wt % to 10 wt %, based on the total weight of the base composition, and is selected from the group consisting of sodium acetate, sodium citrate, trisodium citrate, citric acid, sodium bicarbonate, sodium lactate, trisodium phosphate, disodium phosphate, sodium borate, boric acid, calcium fumarate, sodium succinate, tris-maleate, and any combinations thereof, wherein said electrolyte is present in an amount of 30 wt % to 40 wt %, based on the total weight of the base composition, and is selected from the group consisting of sodium chloride, potassium chloride, magnesium chloride, disodium EDTA, and any combinations thereof, wherein said mild preservative is present in an amount of 15 wt % and 28 wt %, based on the total weight of the base composition, and is selected from the group consisting of esters, phenols, phenoxyethanol, paraben, methyl paraben, butyl paraben, ethyl paraben, propyl paraben, isobutyl paraben, isopropyl paraben, polyquaternium-1, benzalkonium chloride, sorbic acid, potassium sorbate, polyaminopropyl biguanidine, diazolidinyl urea, and any combinations thereof, wherein said lubricant is present in an amount of 35 wt % to 50 wt %, based on the total weight of the base composition, and is selected form the group consisting of is selected from the group consisting of polyols, glycerin, propylene glycol, polypropylene glycol, PEG-400, PEG-8, and any combinations thereof, wherein the photoprotective cosmetic composition is non-irritating to a mammalian eye, and exhibits on a scale of 0 to 3 at least one of a bulbar conjunctiva irritation score of 0.4 or less and a palpebral conjunctiva score of 0.4 or less, wherein said bulbar conjunctiva irritation score and said palpebral conjunctiva score are measured 30 seconds after a drop of said photoprotective composition is instilled into the eye of a user.

2. The non-irritating photoprotective cosmetic composition of claim 1, wherein said water phase has an osmolarity between 175 mOsm/kg and 700 mOsm/kg.

3. The non-irritating photoprotective cosmetic composition of claim 1, wherein said water phase has a pH between 5.5 and 8.5.

4. The non-irritating photoprotective cosmetic composition of claim 1, wherein said water phase has a pH between 6.0 to 7.6.

5. The non-irritating photoprotective cosmetic composition of claim 1, wherein said water phase has a buffer capacity between 0.002 to 0.05.

6. The non-irritating photoprotective cosmetic composition of claim 1, wherein said water phase has a buffer capacity between 0.004 to 0.01.

7. The non-irritating photoprotective cosmetic composition of claim 1, wherein the photoprotective composition has an SPF of 2 to 50.

8. The non-irritating photoprotective cosmetic composition of claim 1, wherein the photoprotective cosmetic composition further comprises one or more components selected from the group consisting of pharmaceutically acceptable carrier, emulsifier, emollient, skin-feel additive, moisturizing agent, film former/waterproofing agent, pH adjuster/chelating agent, preservative, carotenoid, and any combinations thereof.

9. The non-irritating photoprotective cosmetic composition of claim 1, wherein the photoprotective cosmetic composition has a Cumulative Irritation Total (CIT) score of less than 49 in a 14 day cumulative irritation evaluation or cumulative patch test.

10. The non-irritating photoprotective cosmetic composition of claim 1, wherein the photoprotective cosmetic composition has a CIT score of less than 35 in a 14 day cumulative irritation evaluation or cumulative patch test.

11. The non-irritating photoprotective cosmetic composition of claim 1, wherein said electrolyte is sodium chloride.

12. The non-irritating photoprotective cosmetic composition of claim 1, wherein said buffer is trisodium citrate.

13. The non-irritating photoprotective cosmetic composition of claim 1, wherein said preservative is a combination of phenoxyethanol, methyl paraben, butyl paraben, ethyl paraben, propyl paraben, and isobutyl paraben.

14. The non-irritating photoprotective cosmetic composition of claim 1, wherein said lubricant is selected from the group consisting of glycerin, PEG-8, PEG-400, and any combinations thereof.

15. The non-irritating photoprotective cosmetic composition of claim 1, wherein said at least one sunscreen agent is a combination of octyl methoxycinnamate, octyl salicylate, homosalate, and titanium dioxide.

* * * * *